US006416762B1

(12) United States Patent
Joseph-McCarthy et al.

(10) Patent No.: US 6,416,762 B1
(45) Date of Patent: Jul. 9, 2002

(54) ANTI-PICORNAVIRAL LIGANDS VIA A COMBINATORIAL COMPUTATIONAL AND SYNTHETIC APPROACH

(75) Inventors: Diane M. Joseph-McCarthy, Belmont; Lyle D. Isaacs, Cambridge; George M. Whitesides, Newton; Martin Karplus, Cambridge; James M. Hogle, Newton; James Li-wen Cheh, Somerville, all of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/210,282

(22) Filed: Dec. 11, 1998

Related U.S. Application Data

(60) Provisional application No. 60/069,300, filed on Dec. 11, 1997.

(51) Int. Cl.[7] ....................... A61K 39/125; C12P 17/00; G01N 33/543

(52) U.S. Cl. ................................ 424/216.1; 424/217.1; 435/5; 435/117; 435/118; 435/119; 436/91; 436/92; 436/98; 544/3; 544/14; 544/22; 548/100

(58) Field of Search ............................ 435/5, 117–119, 435/DIG. 22, 34; 436/91, 92, 98; 424/216.1, 217.1; 544/3, 14, 22; 548/100

(56) References Cited

U.S. PATENT DOCUMENTS

| | | | | | |
|---|---|---|---|---|---|
| 5,712,171 | A | * | 1/1998 | Zambias et al. | 436/518 |
| 5,750,532 | A | * | 5/1998 | Girijavallabhan et al. | 514/274 |
| 5,874,412 | A | * | 2/1999 | Priebe et al. | 514/34 |

OTHER PUBLICATIONS

Gordon et al., J. Med. Chem. vol. 37, No. 10 pp. 1385–1401, May 1994.*
Miranker, et al., Functionality Maps of Binding Sites: A Multiple Copy Simultaneous Search Method. *Proteins: Structure, Function and Genetics*, 11:29–34 (1991).
US 5,102,457 A (Braig, et al), Apr. 7, 1992, see entire document, especially example 11.
You, A.J., et al., A Miniaturized Array Format for Detecting Small Molecule–Protein Interactions in Cells; Chemistry & Biology, 12:969–975 (1997) See entire document.
Andries, et al., *J. Virol*, 64:1117–1123 (1990).
Elber, R., et al., *J.Am.Chem. Soc.* 112:9161 (1990).

Filman, D.J., et al., *EMBO J.* 8:1567 (1989).

Hogle, J.M., et al., *Science* 229:1358 (1985).
Joseph–McCarthy, D., et al., *Proteins* 29:32–58 (1997).

Phelps and Post, *J. Mol. Biol.* 254:544 (1995).

Rueckert, R.R. and Pallansch, M., *Methods in Enzymol*, 78:315–325 (1981).
Rossman, M.G. et al., *Nature* 317:145 (1985).
Schumacher, T.N., et al., *Science* 271:1854 (1996).
Shuker, S.B., et al., *Science* 274:1531 (1996).
Smith, T.J., et al., *Science* 233:1286.

* cited by examiner

*Primary Examiner*—Bennett Celsa
(74) *Attorney, Agent, or Firm*—Banner & Witcoff, Ltd.

(57) ABSTRACT

The present invention provides structure-based combinatorial libraries of compounds containing the functional group minima of picornaviruses including poliovirus and rhinovirus. The libraries can be used to screen for therapeutical antiviral compounds, e.g., anti-picornaviral capsid-binding compounds.

7 Claims, 13 Drawing Sheets

SPECIFIC MONOMERS INCORPORATED:

SUBLIBRARY 6.2 CONTAINS THREE COMPOUNDS WHICH BIND VIRUS.
LIBRARY 6.2

437

396

384

331

355

343

FIG. 8

ANTI-PICORNAVIRAL LIGANDS VIA A COMBINATORIAL COMPUTATIONAL AND SYNTHETIC APPROACH

This application claims the benefit of U.S. Provisional Application No. 60/069300, filed Dec. 11, 1997.

This work was partially supported by the U.S. government under NIH grants U01 AI-32480, R37 AI-20566 and R01-GM30367. The U.S. government retains certain rights in this invention.

BACKGROUND OF THE INVENTION

1. Field of the Invention

The present invention is broadly directed to structure-based combinatorial libraries, especially a group of compounds containing the functional group minima in picornaviruses including poliovirus and rhinovirus. The libraries provided by the present invention contain candidates of anti-picornaviral capsid-binding compounds which can be therapeutically effective in antiviral treatments.

2. Description of Related Art

Picornaviruses represent a very large virus family of small ribonucleic acid-containing viruses responsible for many serious human and animal diseases (Rueckert, R. R. Virology, 2nd ed. (Fields, B. N. et al., eds.) Raven Press, Ltd., New York, p. 508–548 (1982)). Picornaviruses include four major groups: enteroviruses, rhinoviruses, cardioviruses and apthoviruses. Enteroviruses include polioviruses, Coxsackieviruses, echoviruses, and four numbered enteroviruses.

Poliovirus is the etiologic agent of the disease poliomyelitis in humans, and there are three known serotypes of the virus. The oral poliovaccine, typically given to children, is a mixture of the Sabin strain of the three serotypes of the virus. Mahoney and Leon (the parent strains of Sabin 1 and 3, respectively) are human neurovirulent strains of poliovirus. The oral poliovirus vaccine is safe and effective, yet has two limitations. First, the vaccine is unstable; current vaccines are inactivated by relatively brief (less than 24 hours) exposure to temperatures of 37° C., necessitating transport in a frozen state from the site of manufacture to the locale where they are administered. Second, the vaccine occasionally reverts to virulence in vaccine recipients; the reverted virulent virus may also be passed to other individuals who come into contact with the recipient in whom the vaccine has reverted.

The human rhinoviruses consist of at least 100 serotypes and are the primary causative agents of the common cold. Because of the large number of serotypes, development of a vaccine is problematic; antiviral agents may therefore be the best approach to treatment. The Coxsackieviruses (24 group A serotypes, 6 group B serotypes), echoviruses (34 serotypes) and human enteroviruses (four serotypes), are associated with a wide range of human diseases including summer flus, diarrhea, meningitis, hepatitis, pneumonia, myocarditis, pericarditis, and diabetes (Melnick, J. L. Virology, 2nd ed. (Fields, B. N. et al., eds.) Raven Press, Ltd., New York p549–605). These infections occur sporadically in the general population, but are becoming more common among children in day care and their parents and siblings. Other important members of the picornavirus family include human hepatitis A virus, Theiler's murine encephalomyelitis virus, foot-and-mouth disease virus, and mengovirus.

Several crystal structures of poliovirus and rhinovirus capsids have been solved by X-ray diffraction. The X-ray structures of poliovirus P1/Mahoney (Hogle, J. M., et al., Science 229:1358 (1985)); poliovirus P3/Sabin (Filman, D. J., et al., EMBO J. 8:1567 (1989)); rhinovirus 14 (Rossman, M. G., et al., Nature 317:145 (1985)); rhinovirus 1A (Smith, T. J., et al., Science 233:1286 (1986)); and rhinovirus 16 (Oliveira, M. A., et al., Structure 1(l):51–68 (1993)) are strikingly similar, although poliovirus and the rhinoviruses are currently classified in different genuses. Experimental results have revealed that there is a binding site in the poliovirus structure which usually binds a lipid-like molecule (Filman, D. J., et al., EMBO J. 8:1567 (1989)). When a drug is bound in this site in poliovirus or rhinovirus, the virus is stabilized, and in some cases. infection is prevented (McSharry, J. J., et al., Virology 97:307 (1979); Smith, T. J., et al., Science 233:1286 (1986); reviewed in Zhang, A., et al., Virology, 3:453 (1992)). The functional group minima of picornavirus capsid proteins have been determined via computational analysis of a ligand binding site (D. Joseph-McCarthy et al., 1997, Proteins 29:32).

The existing drugs which are used against the viruses described above are only moderately effective. Available drugs are typically effective against only a limited subset of the rhinovirus serotypes. In general, the available drugs have either failed to demonstrate sufficient prophylactic effect or are converted in the body into inactive metabolites. Furthermore, current drugs have all been derived from the same parent compound that was found through large-scale random screening of known chemicals for activity against the virus, a very expensive and time-consuming process. A need continues for additional drugs with better efficacy, and with efficacy against pathogenic picornaviruses.

SUMMARY OF INVENTION

It is an object of the invention to provide a composition which is a candidate anti-picornavirus capsid-binding compound.

It is another object of the invention to provide a library of compositions useful for screening for anti-picornavirus capsid-binding compounds.

It is yet another object of the invention to provide methods of making the compositions and the libraries of the compositions provided in the present invention.

These and other objects of the invention are provided by one or more of the embodiments provided below.

In one embodiment of the invention there is provided a composition which comprises two aromatic monomers and a spacer monomer, wherein the two aromatic monomers are covalently linked through X to the spacer monomer, where X is S or O, and the aromatic monomer and the spacer monomer are functional group minima of picornaviruses.

In another embodiment of the invention there is provided a method of making the composition provided by the present invention which comprises the steps of mixing equimolar amounts of one or more aromatic monomers to form a mixture, incubating a solution of one or more dibromide spacer monomers with the mixture to form an organic phase, washing and concentrating the organic phase.

The present invention provides libraries of compounds which are candidates for anti-picornaviral capsid-binding compounds. Such compounds provide therapeutic benefits in anti-picornaviral treatment. The present invention also provides methods for making such libraries.

DETAILED DESCRIPTION OF THE INVENTION

Figure 1:
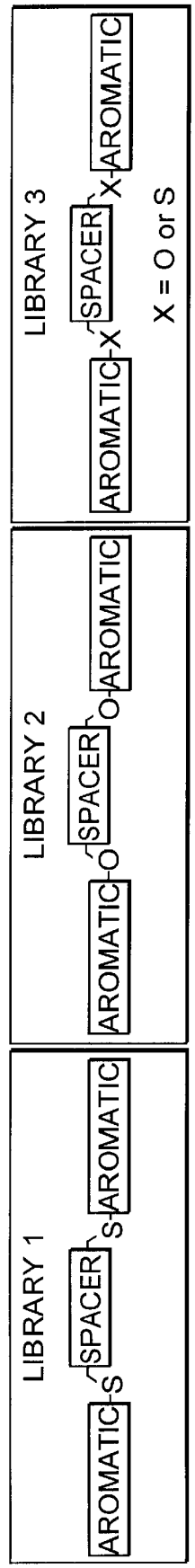
FIG. 1 shows a schematic of library ligands of the present invention.

The present invention is broadly directed to structure-based combinatorial libraries containing anti-picornaviral capsid-binding compounds. Such compounds can be therapeutically effective in anti-picornaviral treatments.

The libraries provided by the present invention are designed based on computational methods. For picornaviruses, e.g., poliovirus and rhinovirus, functional group minima for regions of the known drug binding pockets, in the capsids, can be calculated and mapped according to computer programs readily available in the art, e.g., the Multiple Copy Simultaneous Search (MCSS) program (Miranker et al., *Proteins*, 11: 29, 1991; Evensen et al., MCSSv2, Harvard University, Cambridge, Mass., 1997).

In a typical MCSS run, N copies of a given functional group are randomly distributed in a specified site, where N is usually between 1000 and 10,000. Functional groups are typically simple small molecules. A large number of functional groups are available in the current implementation of MCSS to picornaviruses, e.g., poliovirus and rhinovirus, and additional functional groups can easily be included.

Functional group minima can be determined via any means known in the art. Using MCSS, copies of functional groups can be simultaneously and independently energy minimized in the field of a fixed protein, with a computer program readily available in the art, e.g., a modified version of the program CHARMM. By the time-dependent Hartree approximation (Elber, R., et al., J. Am. Chem. Soc. 112:9161 (1990)), each copy of functional groups will feel the full force field of the protein but the copies do not interact with each other. Specifically, the copies of the group are simultaneously subjected to steps of minimization, e.g., 500 steps of steepest decent minimization, followed by steps of Powell minimization, e.g., 500 steps of Powell minimization and then 9 cycles of 1000 steps of Powell minimization each, for a total of 10,000 minimization steps. Thereafter minimization, e.g., about every 1000 steps of minimization, duplicate functional group minima are discarded. In addition, functional group minima are deleted from the system after each cycle except for the first, if their interaction with the protein energy is too high as determined by a series of user specified energy cutoffs. After the final cycle, the remaining minima may be sorted by interaction energy and their coordinates and interaction energy may be recorded to a file. Since the protein competes with solvent for binding functional groups, functional group minima whose free energy of binding to the protein is less than their free energy of solvation are preferred for the structure-based combinatorial libraries provided in the present invention.

Different approaches could be taken to construct chemically sensible drug molecule candidates for the structure-based combinatorial library of the present invention. One approach is to connect the desired functional group minima via placing linker carbon atoms between selected minima and optimizing the position of the link atoms. Typically, each library compound is composed of three connected monomers, e.g., two aromatic monomers and a spacer monomer. The specific monomers that are selected for each of the three monomer positions of the compounds are determined to a large extent by calculations of computer programs readily available in the art, e.g., MCSS.

Figure 2A:
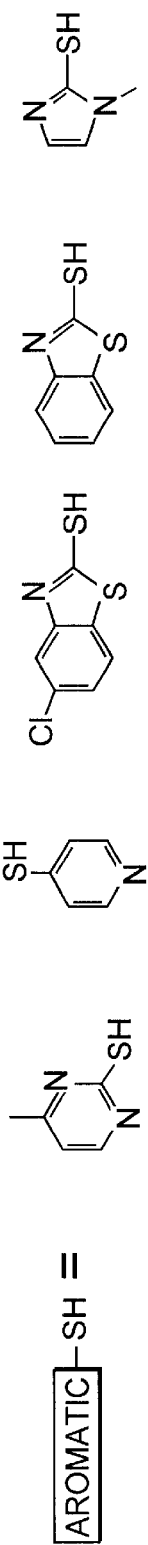
FIG. 2 shows a schematic of the specific monomers that are positioned in the ligands.
Figure 2B:
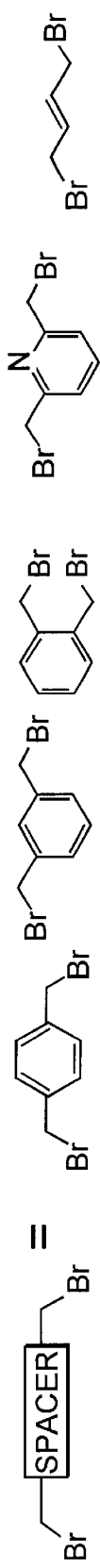
Figure 2C:
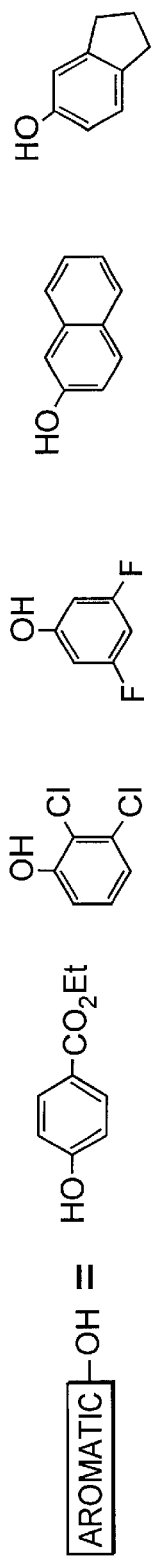
Figure 3:
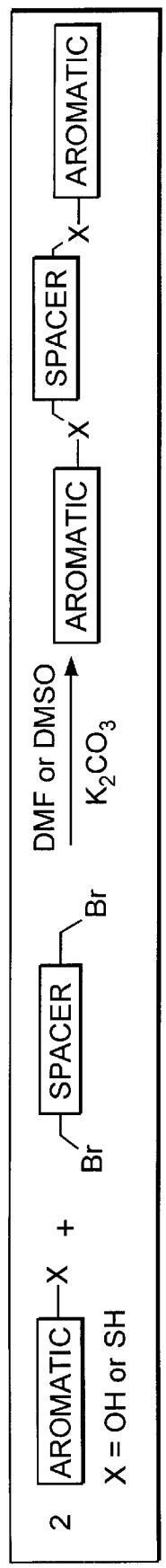
FIG. 3 shows a schematic of the combinatorial synthesis scheme of the present invention.
Figure 4A:
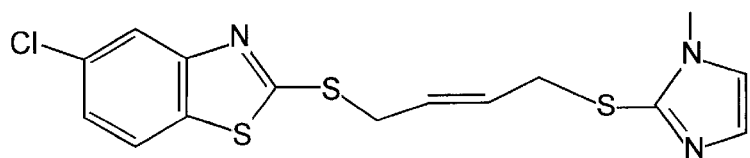
FIG. 4 shows structures of compounds that have been screened from a library of the present invention that bind to the Mahoney poliovirus capsid.
Figure 4B:
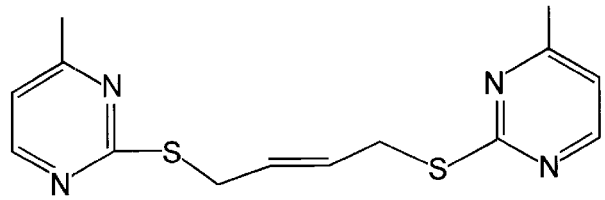
Figure 4C:
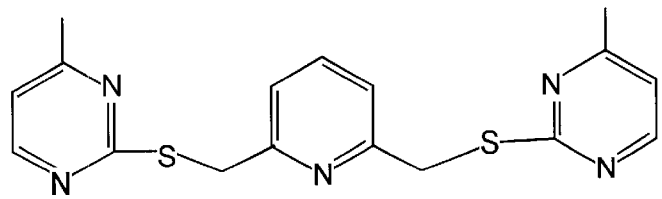
Figure 4D:
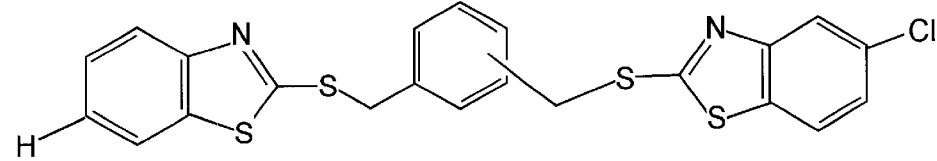
Figure 4E:
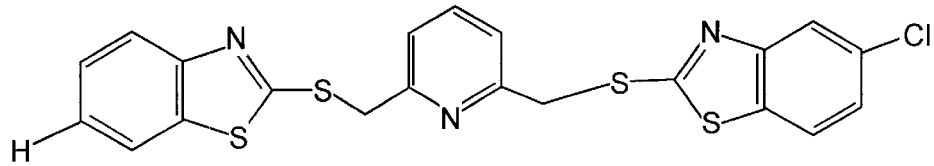
Figure 4F:
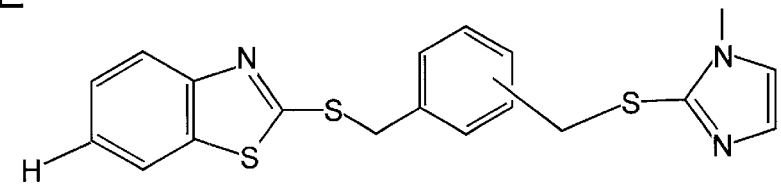
Figure 4G:
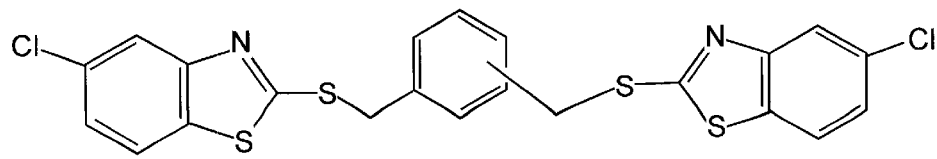
Figure 4H:
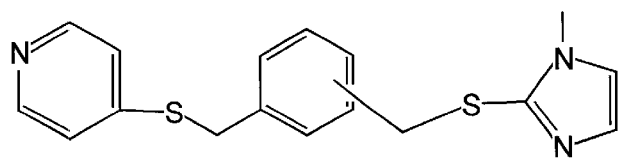

Monomers may be aromatic alcohols or aromatic sulfhydryls. The general structure of the monomers are shown in FIGS. 1–3. The aromatic ring structure may be a five-membered ring, a six membered ring or a five membered ring fused to a six membered ring or two six membered rings fused.

The aromatic alcohols may be monocyclic or polycyclic with one or more substituents in the ortho, meta or para positions on the ring. The substituents must be non-electrophilic relative to the spacer (e.g., $BrCH_2RCH_2Br$) monomers, and may be hydroxyl, methoxy, ester, nitro, or thiol groups; halogens (such as Cl, Br, F, I); or carbon atoms. If one ring structure is utilized it is a five or six membered ring. If two ring structures are utilized, one may be a six membered ring and the second may be a five membered ring fused to the six membered ring. Alternatively, two six membered rings may be fused. The aromatic alcohol may also have one or more heteroatoms (nitrogen, sulfur or oxygen) substituted for carbon atoms within the ring(s). Monomers with saturated ring structures, e.g., cyclohexyl or two fused cyclohexyl rings, are also possible. The hydroxyl group substituent may be attached to any of the available ring atoms.

In another embodiment of the present invention, aromatic sulfhydryls may be utilized as the monomers in the library design. The aromatic sulfhydryls may be heterocyclic and contain one or more heteroatoms in a single ring structure. If one ring structure is utilized it is a five or six membered ring. If two ring structures are utilized, one may be a six membered ring and the second a five membered ring, or alternatively, two six membered rings may be fused together. Nitrogen and oxygen may be substituted for carbon atoms. Further, substituents may be present on the sulfhydryl aromatic ring structure as described above for the aromatic alcohol monomers.

The monomers are covalently linked by spacer compounds as shown in FIGS. 1–3. The monomers and spacer compound are linked through an oxygen or sulphur atom.

The spacer compound is a symmetric bis-(bromo methyl) arene or alkane. For the oxygen linked library there must be double bonds one carbon removed from the bromide substituents. Since thiols are more nucleophilic than alcohols, double bonds are not required in the linkers for the thiol library. The bromides are expected to be separated by a carbon chain length of 2 to 5 atoms. Further, there may be other small groups attached to the aryl or allyl groups. Such groups include hydroxyl, methoxy, methyl, ester, nitro, or halogens. In place of dibromides, dichchlorides, -iodides, or -tosylates could also be used as spacer monomers.

The synthesis of the library compounds can be carried out by any means known in the art. For example, solution phase chemistry. The combinatorial synthesis scheme is shown in FIG. 3. Usually, equimolar amounts of one or more desired aromatic monomers will be dissolved to form a solution mixture. An equimolar solution of one or more desired spacer monomers, i.e., dibromide spacers will be added to the solution mixture of the aromatic monomers in the presence of $K_2CO_3$. The resulting mixture may be incubated for a period of time, e.g., 24 hours. The precipitate formed during the reaction, e.g., KBr can be filtered out and the resulting solution can be concentrated to dryness at reduced pressure. The residue may be partitioned, e.g., between EtOAc and aqueous $NaHCO_3$ (saturated). The organic phase may be further washed, dried, and concentrated at high vacuum. Any unreacted starting materials, e.g., dibromide could be removed from the mixture by aqueous acid extraction to pull the basic library members into the acid layer or by adding beads with a thiol, e.g., dithiothreitol attached, or beads with a bromide or other halide attached.

The structure-based combinatorial libraries provided by the present invention could also be synthesized using a split synthesis approach so that up to three related compounds are separately compartmentalized, i e., library as array. The library as array may be synthesized in microtiter plates or any other container having a microtiter plate like arrangement. Usually, a stoichiometric amount of $K_2CO_3$, two identical or different monomers, and a dibromide spacer monomer is dispensed into each well of a plate. The dispensing of monomers and spacers into each well of a plate may be pre-coded by any means known in the art so that monomer and spacer compositions of a compound in each well are known. For example, a stoichiometric amount of a single pre-determined monomer may be dispensed into each well of a single horizontal row in a plate; while a stoichiometric amount of a single predetermined monomer is dispensed into each well of a single vertical column in a plate; and a stoichiomatric amount of a single pre-determined spacer is dispensed into each well of a plate. As a result, each well will contain up to three related compounds with the monomers connected in three different ways, e.g., M1-Spacer-M2, M1-Spacer-Ml, and M2-Spacer-M2.

The viral binding ability of the compounds provided by the present invention can be assessed by any means known in the art, e.g., cell-based assays, immunoprecipitation assays, fluorescence assays, and crystallographic assays. For example, the minimum inhibitory concentration (MIC) of the compounds can be determined via cell-based assays. An MIC value is usually measured by a standard method, as described in Andries et al., (*J. Virol*, 64:1117–1123, 1990). Briefly, serial dilutions of the compound of the present invention are added to solutions containing approximately 100 tissue culture infectious doses of viruses, and the resulting mixtures are added to subconfluent layers of HeLa cells in a microtiter plate. The MIC is taken as the lowest concentration of a compound that protects 50% of cells from cell death or cytopathic effect. The lower the MIC value of a compound, the higher efficacy of the compound and presumably the viral binding ability of the compound.

The viral-binding compounds in the libraries of the current invention can be used to stabilize capsids of picornaviruses and other related viruses by binding to the virus. The compounds can thus be used to stabilize unstable forms of virus for experimental studies. The compounds can also be used to increase the stability, particularly the thermal stability, of existing poliovirus vaccines or vaccines for related viruses. In addition, the compounds can be used to prevent viral changes necessary for cell entry. The compounds can also be used to terminate replication of live vaccine virus after sufficient time has elapsed to induce an immune response in an individual, minimizing the risk of vaccines shedding reverted virus which are neurovirulent. The compounds can additionally be used for prophylactic treatment of non-vaccinated family members of vaccines. The compounds can further be used for prophylaxis and therapeutic treatment of infection with rhinoviruses, enteroviruses, Coxsackieviruses, echoviruses, and other picornaviruses with accessible binding sites.

The following examples are provided for exemplification purposes only and are not intended to limit the scope of the invention which has been described in broad terms above.

EXAMPLE 1

This Example Demonstrates the Synthesis of Library 1 as Shown in FIG. 1

A mixture of a group of five desired monomers (FIG. 2a) at 0.6 mmol each was dissolved in 20 ml DMF under $N_2$. Solid $K_2CO_3$ of 0.829 g (6 mmol) was added to the solution which was stirred at RT for 5 min. To the resulting mixture an equimolar solution of a group of five dibromide spacer monomers (FIG. 2b) at 0.3 mmol in 15 ml DMF was added. The reaction was continued at room temperature for 24 hours. The precipitated KBr was filtered out. The resulting solution was concentrated to dryness at reduced pressure. The residue was partitioned between EtOAc and aqueous $NaHCO_3$ (saturated). The organic phase of the solution was further washed with $H_2O$ and aqueous NaCl (saturated.), dried over $MgSO_4$, and concentrated. The resulting amber colored material was dried at high vacuum. Any unreacted dibromide could be removed from the mixture by aqueous acid extraction (thereby pulling the basic library members into the acid layer) or by adding beads with a thiol (e.g., dithiothreitol) attached. Assuming that all of the reactions occurred as planned, the library is expected to consist of 75

$$[\text{Formula 1:} \quad m\sum_{i=1}^{n} i$$

where m is the number of spacer monomers (here 5) and n is the number of thiol monomers (here 5)] compounds including all possible unique combinations of the allowed monomers.

EXAMPLE 2

This Example Demonstrates the Synthesis of Library 2 as Shown in FIG. 1

A mixture of five desired monomers (FIG. 2c) at 0.6 mmol each and five desired dibromide spacers (FIG. 2b) at 0.3 mmol each were dissolved in 4 ml DMF under $N_2$. Solid $K_2CO_3$ of 0.415 g (3 mmol) was added to the solution which was subsequently stirred at 57° C. overnight. The reaction mixture was then diluted with water and extracted with $Et_2O$ and EtOAc. Subsequently, the organic phase of the reaction mixture was washed with 2M NaOH, dried over $K_2CO_3$, and concentrated. The resulting amber colored material was then dried at high vacuum. Assuming that all of the reactions occurred as planned, the library is expected to consist of 75 [Formula 1 above, where m is the number of spacer monomers (here 5)] and n is the number of hydroxyl monomers (here 5))compounds including all possible unique combinations of the allowed monomers.

EXAMPLE 3

This Example Demonstrates the Synthesis of Library 3 as Shown in FIG. 1

A mixture of five desired thiol monomers (FIG. 2a) at 0.6 mmol each, five desired phenol monomers (FIG. 2c) at 0.6 mmol each as well as the five desired dibromide spacers (FIG. 2b) at 0.3 mmol each were dissolved in 4 ml DMSO under N2. Solid $K_2CO_3$ of 0.829 g (6 mmol) was added to the solution which was then stirred at 57° C. overnight. The reaction mixture was subsequently diluted with water, extracted with $Et_2O$ and EtOAc. The organic phase of the reaction mixture was washed with 2M NaOH, dried over $K_2CO_3$ and concentrated. The resulting amber colored material was then dried at high vacuum. Assuming that all of the reactions occurred as planned, the library is expected to consist of 275 [Formula 1 (above), where m is the number of spacer monomers (here 5) and n is the number of thiol monomers plus the number of hydroxyl monomers (here 5+5=10)] compounds including all possible combinations of the allowed monomers.

EXAMPLE 4

This Example Demonstrates the Synthesis of Library as Array in Microtiter Plates The procedure to synthesize library as array in a 8×12 microtiter plate is as follows: 1) to each well of the plate, adding a stoichiometric amount of $K_2CO_3$, it may be necessary to make an aqueous solution to make the dispensing easier, 2) to each well of a horizontal row, adding a stoichiometric amount of a single pre-determined monomer, changing the identity of the monomer for each horizontal row, 3) to each well of a vertical column, adding a stoichiometric amount of a single pre-determined monomer, changing the identity of the monomer for each vertical column, 4) to each of the 96 wells, add a stoichiometric amount of a single pre-determined spacer dibromide in DMF (different dibromides would be used on separate 96 well plates).

EXAMPLE 5

This Example Confirms the Activity of the Combinatorial Libraries and Demonstrates the Screening Procedures The library of 75 compounds described in Example 1 was screened for potential binders to the Mahoney poliovirus capsid. FIG. 2 shows the eight compounds found in the assay to screen for viral binding compounds. The cell free assay is described as follows.

1) Formation of Virus-Compound Complexes.

Figure 5:
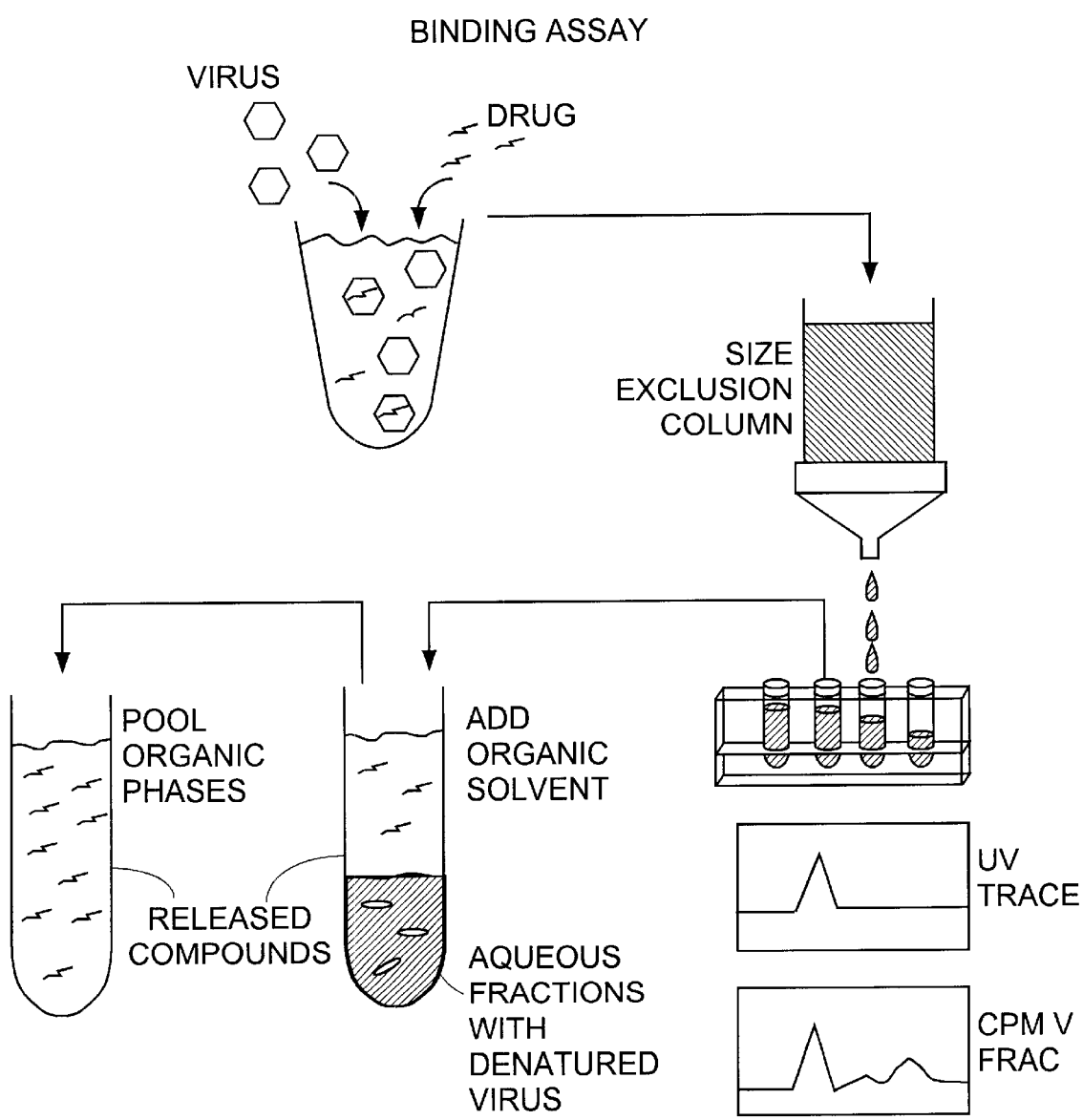
FIG. 5 shows a schematic drawing of the virus binding assay.

The initial phase of the assay involves the incubation of virus with libraries of compounds to allow for the specific interaction between the compounds and virus. Poliovirus (P1/Mahoney, or P1/M) is grown in HeLa cells and purified by differential centrifugation and CsCl density gradient fractionation according to standard methods (Rueckert, R. R. and Pallansch, M., Methods in Enzymol. 78:315–325 (1981)). The virus is stored frozen in phosphate buffered saline (PBS) at −80° C. until use. Stock solutions of the virus are in PBS, while mixtures of potential ligands are dissolved in DMSO. These stock solutions are diluted such that all incubations are carried out at a final DMSO concentration of 5% in PBS. Final volumes ranged from 0.5 to 1.0 mL. Once mixed, the incubations were left at room temperature for one to four hours or kept at 4° C. overnight (See FIG. 5 for schematic).

The sensitivity of the assay is largely dictated by two factors: (1) the amount of virus used, which determines the number of available virus binding sites, and (2) the current detection limit of mass spectroscopy (MS). For our electro-spray mass spectrometer, this limit is 50 picomole/25 µL or 2 µM. In the case of MALDI-TOF MS, the mass spectrometer at our disposal has a limit of approximately 1 picomole. Using our MALDI-TOF MS, therefore, to select ten compounds from a library of indefinite size requires 10 picomoles of viral sites (see below for recovery rates). A typical experiment requires between 0.1 and 0.8 mg of virus in 0.5 mL incubation mixture.

Detection of virus-compound complex formation largely depends upon two factors. First, the concentration of the compound in the incubation must be above a critical threshold. Existing anti-picornaviral compounds work in the micromolar to nanomolar range. The estimated concentration of compound in the typical stock solutions of existing libraries is $6 \times 10^{-3}$M. Screens have been carried out with the total concentration of compound in the incubation ranging from 10 to 350 µM. Complex formation can be driven by increasing the number of drug molecules per viral binding sites. In so doing, a competition results between compounds in the library for the available binding sites. Those compounds which have the highest affinity for the pocket, i.e., viral binding site will easily compete out the weaker binders and the excess compound ensures that the equilibrium of binding is shifted towards complex.

2) Purification of Virus-Compound Complexes.

Virus-drug mixtures are loaded onto a size exclusion column (1.4 cm diameter×8.4 cm height) having a Sephacryl S-200 or S-300 matrix (Pharmacia) to separate virus-drug complexes from unbound drug. The running buffer is 5% DMSO in PBS. One mL fractions are collected at 0.5 mL/min. Identification of fractions containing the void volume, and therefore possibly containing viruses bound with compound, is accomplished with a Pharmacia Uvicord SII UV monitor which measures the OD280 of the material as it is pumped out of the column (See FIG. 5 for schematic).

3) Extraction and Concentration of Virus-Bound Drug.

Fractions containing virus bound with compounds are mixed with a double volume of ethyl acetate, vortexed for 30 seconds, then centrifuged for 10 minutes at 12,000×g. At this point the viruses will be completely denatured. Previously virus-bound drug is released, and will partition into the ethyl acetate phase. The upper organic phase is separated from the aqueous phases. The organic phase containing the compounds is dried in a centrivap (See FIG. 5 for schematic).

4) Preparation of Sample for MS.

A small volume (50 µL) of an organic solvent is added to the tube containing the dried sample. Which solvent should be used depends upon the MS technique used for the analysis. For MALDI-TOF MS, the solvent is acetonitrile or THF. In the case of electro-spray MS, it is ethanol. After the addition of solvent, the tube containing the sample is vortexed. At this point, the concentration of each virus-bound compound is at least 2 µM, high enough for detection by electro-spray MS or MALDI-TOF MS. The decision between electro-spray or MALDI-TOF depends upon the material in the sample.

5) Detection of Virus Bound Compounds.

A) Optimization of Assay Conditions with Radiolabeled Compounds.

The conditions of this assay were optimized using the radiolabeled compound R77975 (Janssen Pharmaceuticals). The radiolabel enabled us to track the amount of drug recovered at each step of the assay. Briefly, in a siliconized tube 240 ML of a preparation containing 2.32 mg/mL of viral binding sites, i.e., P1/M in PBS was mixed with 15.8 mL of 2.5×10$^{-4}$M $^3$H-R77975 in DMSO. The incubation volume was brought up to 500 mL and the DMSO content was 5% in PBS. The ratio of drug to viral binding sites or pockets was 1:1. This mixture was left at room temperature for 2 hours, then loaded onto the size exclusion column. Fractions 6 through 11 contained the virus as determined by UV trace.

To determine the yield of $^3$H-R77975 in each fraction, 100 mL of each fraction was transferred to a 7 mL scinitillation vial containing Ecoscint A (National Diagnostics) and counted in a Beckman 5000TD scintillation counter. 33% of the input labeled compound was found to be in the void volume and was bound to the virus. Nearly 100% of this material was recovered after the ethyl acetate separation. Subsequent concentration of this sample in the centrivap yielded 77% of the extracted compound. The overall recovery of drug was 26%.

To show that the binding of R77975 is specific, a competition experiment was done with R78206, a tighter binding compound, and the results showed that the assay is capable of selecting the best binder out of a mixture of compounds. 57 μg of P1/Mahoney poliovirus was incubated in a PBS 5% DMSO solution containing 4×10$^{-9}$ moles of$^3$ H-R77975 and R78206 respectively, corresponding to a drug to pocket ratio of 10:1 for each compound. The concentration of drug used in the incubation was 8 μM. Under these conditions only R78206 is expected to be bound to virus since its minimum inhibitory concentration (MIC) is 8 nM, compared to 3 μM for R77975. After an incubation time of 2 hours at room temperature, the mixture was run through the column. By counting the amount of radioactivity in the void volume, it was possible to determine whether any of the R77975 bound to the virus. As expected, there was no radioactivity associated with virus in the void volume.

B) Assay Detects Binding of Drug with nM MIC.

R78206 (Janssen Pharmaceuticals), a more potent analog of R77975, was incubated with viral binding sites, i.e., P1/M. Previous work had shown that this compound bound to the virus inside the hydrophobic pocket of VP1 and prevented viral replication in vitro. In this incubation, the moles of R78206 equaled the moles of pocket sites. The concentration of R78206 in the incubation was 8 μM. R78206 has a molecular weight of 383 and gave an [M+H]+ peak of 384 in the MALDI-TOF mass spectrum from this experiment. As an additional control, this experiment was repeated with no virus present to ensure that the signal was not simply due to some small amount of residual unbound drug, and as expected, no peak was observed at 384.

C) Assay Detects Binders in a Mixture of Compounds with MIC Values Ranging From nM to μM.

Figure 6:
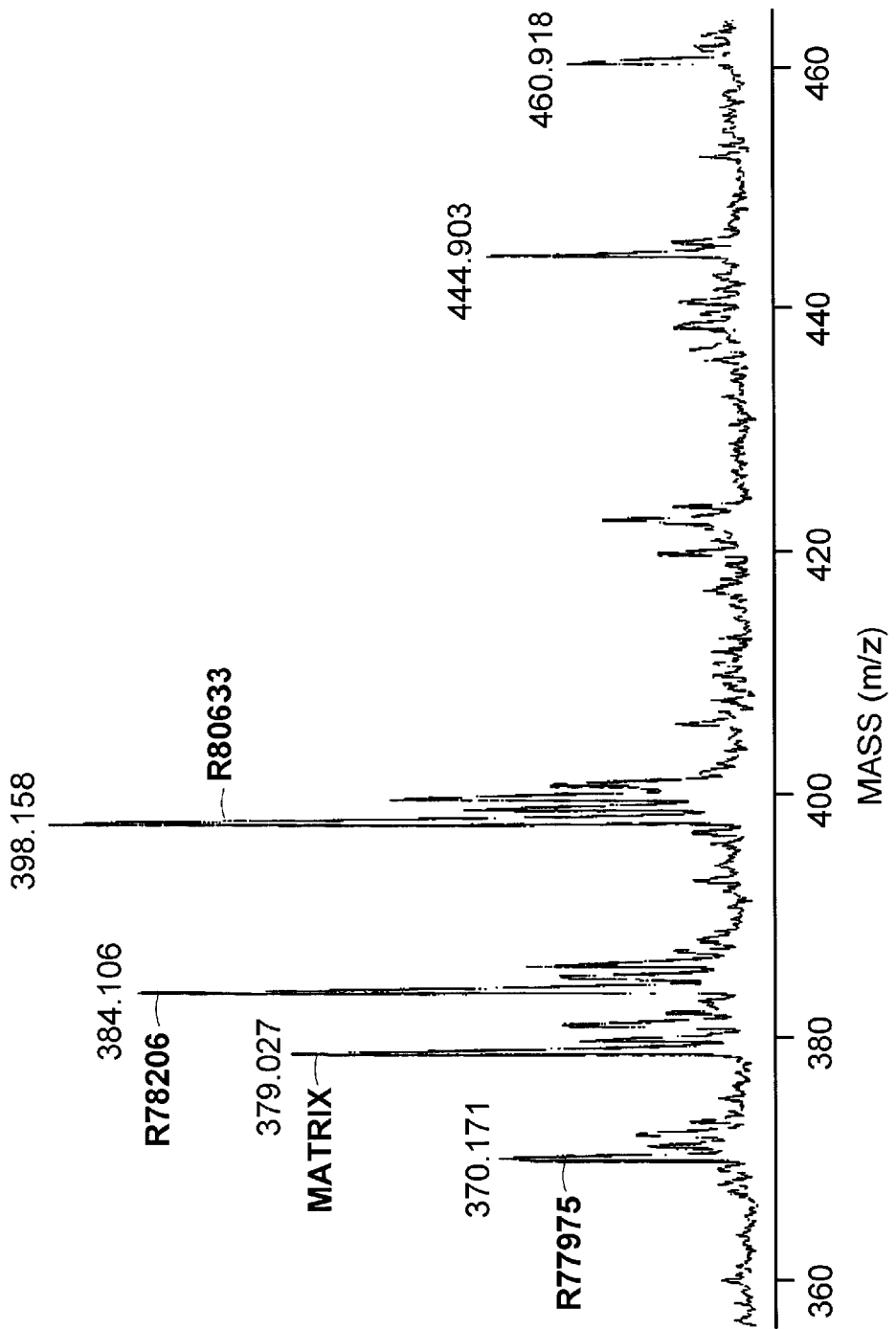
FIG. 6 shows a mass spectroscopy analysis of drugs released from virus.

In this experiment, three Janssen analogs, R77975, R78206, and R80633, were incubated with virus. All compounds were present in equimolar amounts and there were exactly enough sites to bind all of each compound. To be more precise, there were 6×10$^{-9}$ moles of binding sites and 2×10$^{-9}$ moles of each compound. In a 500 μL volume, the drug concentration was 4 μM. After an overnight incubation at 4° C., the incubation was assayed and the resulting MALDI-TOF mass spectrum contained only three peaks corresponding to the three compounds (FIG. 6).

D) Ability of Assay to Discriminate Between Binders and Non-binders

To ensure that the binding of drug to virus was specific, we constructed a test library containing two drugs with proven anti-viral activity, R78206 and R80633, alongside a cocktail of structurally related compounds with no expected ability to bind virus (as shown in earlier crystallographic experiments). In this incubation, each compound was present in an equimolar amount and there were exactly enough pockets to bind all of each compound. The MALDI-TOF spectrum from this experiment indicated the expected peaks for R78206 and R80633. Of the other five compounds, a peak was detected for one, indicating that it may in fact be a weak binder. All other parent molecular weight ion peaks were absent.

E) Library A +virus.

A library of 75 potential ligands was synthesized using combinatorial chemistry as described above. The design of this library was based upon extensive computer modeling on poliovirus and rhinovirus (Joseph-McCarthy, D. et al., Proteins 29:32–58 (1997)). An incubation was set up such that the concentration of the library was 15-fold greater than the concentration of virus binding sites. Specifically the concentration of library A was 3.24×10$^{-4}$ M in the incubation, while the concentration of virus sites was 2.16×10$^{-5}$ M. Given the amount of virus relative to compounds used in this assay, there should be enough sites to bind up to approximately 5 compounds.

After subjecting this incubation to the binding assay, the concentrated sample was analyzed by both electrospray and MALDI-TOF MS. In the MALDI-TOF spectrum, there were in fact 5 peaks and 1 weak peak that could correspond to compounds in the library. The electrospray spectrum showed five relatively strong peaks which corresponded to compounds in the library as well, three of which were also present in the MALDI-TOF spectrum. There were 4 additional weak peaks in the electrospray mass spectrum that could correspond to compounds in the library, one of which also appeared as a weak signal in the MALDI-TOF spectrum. In total, 7 reasonable peaks from both sets of spectra that could correspond to library compounds were identified. These individual compounds will now be synthesized and confirmed for binding by using more stringent assays (e.g., immunoprecipitation, cell-based, fluorescence, and crystallography).

In order to confirm the results from the Library A screen, a six compound library that is a subset of Library A was combinatorially synthesized. This six compound library contains two of the potential Library A binders from the previous screen. One milligram of virus was incubated with a PBS/5% DMSO solution containing 5.7×10$^{-4}$M of the six compound library (roughly 10 μM per compound), corresponding to a library to pocket ratio of 4:1. After an overnight incubation at 4° C., the incubation was run through the size exclusion column and fractions 7 to 13 were extracted, concentrated, and analyzed by mass spectroscopy. The library is expected to contain compounds with molecular weights 280, 292, 304, 367, 379, and 454. The spectrum identified four potential binders.

F) A Hybrid Split-Pool Synthesis Approach.

An alternative approach to screening compounds in combinatorial libraries involves the generation of multiple libraries, each containing approximately 5 to 10 compounds. This approach avoids difficulties in controlling the relative representation of individual members of the larger (approximately 100 compound) libraries and the relatively low signal to noise ratio in mass spectroscopic analyses when larger libraries are used.

Figure 7:
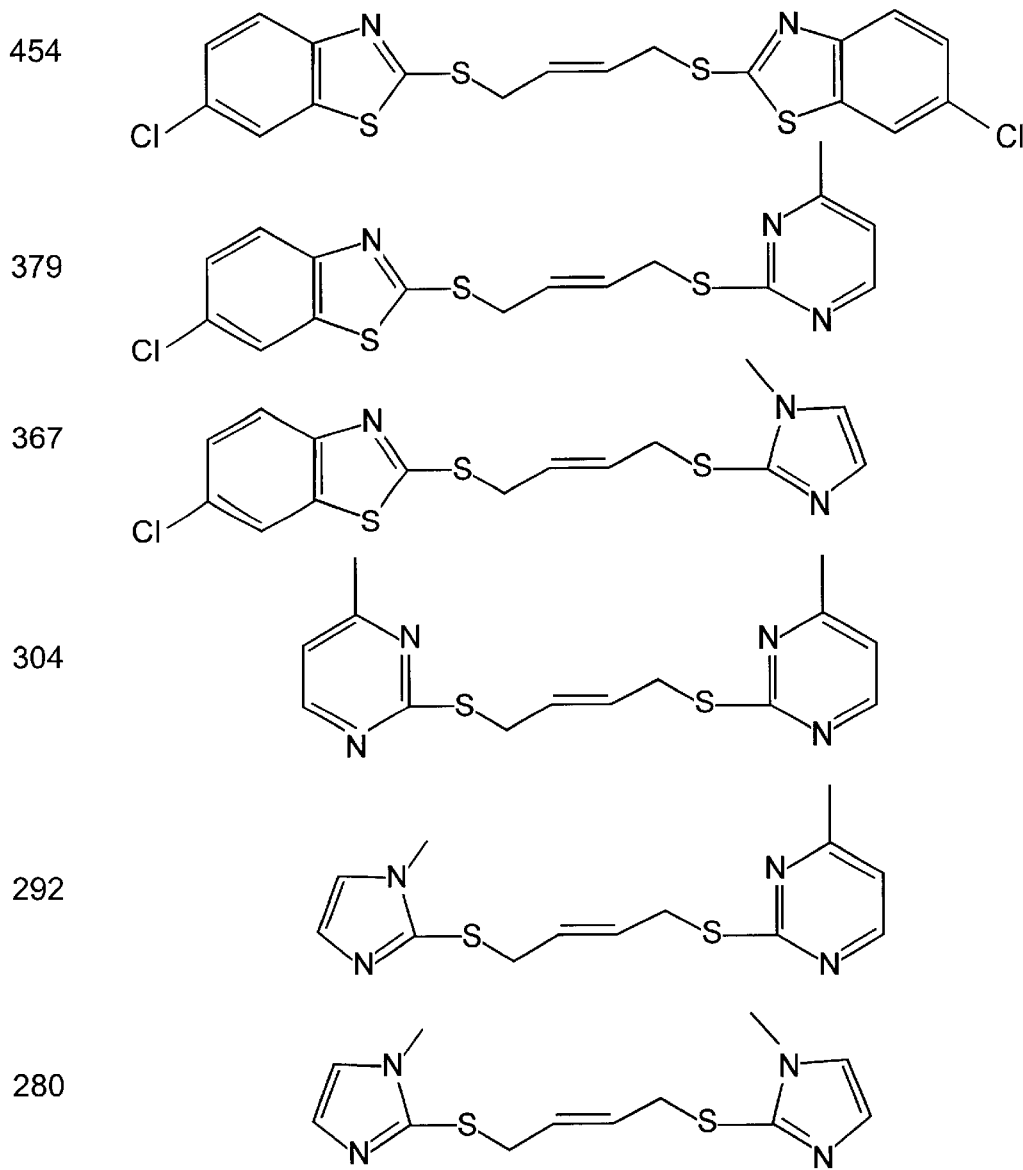
FIG. 7 shows the members of Library 6.1 and mass spectroscopy of a virus binding assay of that library.
Figure 7:
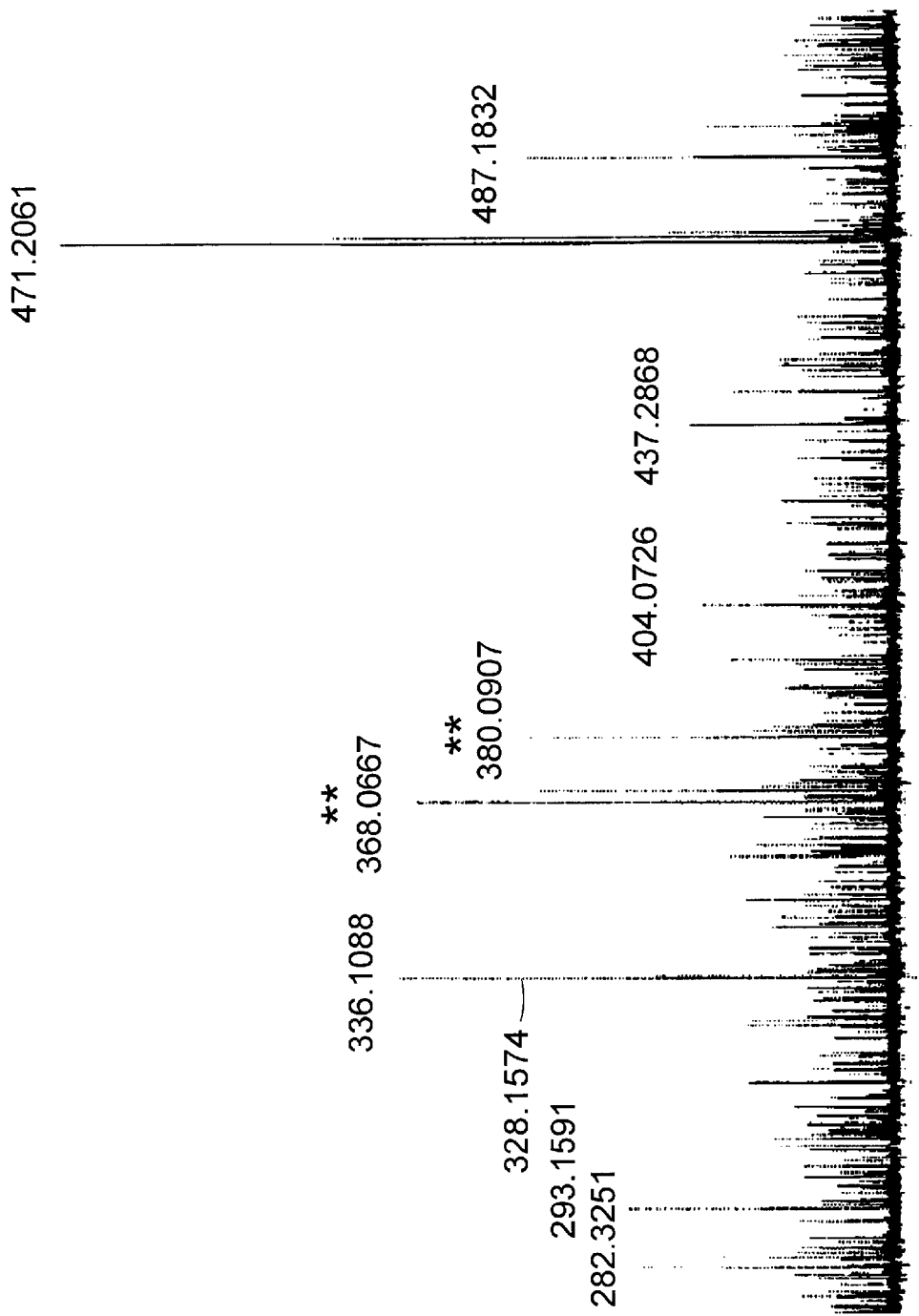
Figure 8:
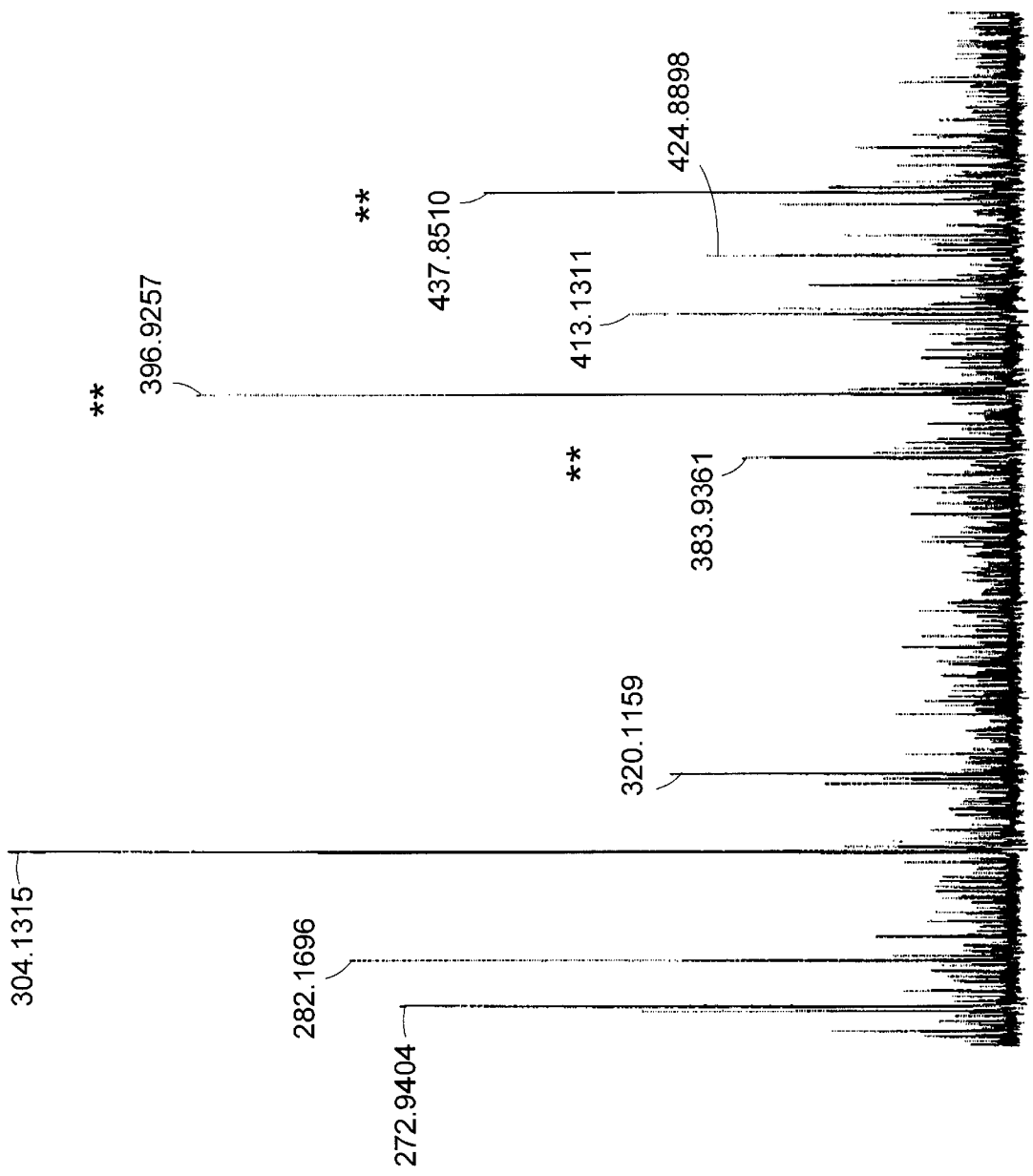
FIG. 8 shows the members of Library 6.2 and mass spectroscopy of a virus binding assay of that library.

To test this approach, two small libraries containing six compounds each, termed Libraries 6.1 and 6.2, respectively, were synthesized (FIGS. 7 and 8) and tested for viral binding. The mass spectroscopic assay provided convincing evidence that two compounds from Library 6.1 and three compounds from Library 6.2 bind to the virus (FIGS. 7 and 8). In addition to increased control over the synthesis and improved signal to noise in the assay, the hybrid split-pool approach has the advantage that each of the sublibraries may be designed to ask a specific question about modification of a portion of the candidate ligand. Indeed, Library 6.1 was originally designed to explore the consistent hits from library A, and Library 6.2 was designed to address the role of large aromatic versus small aliphatic linkers in the central region of the molecule.

Relatively large numbers of such small libraries may be synthesized simultaneously, and the results analyzed by the sparse matrix and limited factorial approaches that have become popular in other complex multidimensional searches, including crystallization (Schumacher, T. N. et al., 1996, Science 271: 1854; Shuker, S. B., et al., 1996, Science 274: 1531; Smith, T. J. et al., Science 233: 1286). The results of the first round could then be used to design the next generation of multiple small libraries that either probe promising areas of ligand space on progressively finer matrices, or address problems (e.g. solubility or toxicity) which have been identified in the previous round.

G) A Functional Assay for Screening Libraries. Although the mass spectrometry assay has proved very useful in identifying ligands that bind virus it does not address the question of whether the observed binding is functional. Therefore, a secondary functional assay was developed. A test for the ability of compounds to inhibit viral infectivity, for example a tissue culture assay such as that described by Grant, R. A. et al., 1994, Curr. Biol. 4: 784 (the method of which is herein incorporated by reference) may be used. However, this assay is delicate and somewhat cumbersome and requires rigorous purification of ligands to avoid toxicity of reactants and by-products. An indirect assay that measures the ability of ligands to interfere with the conformational conversion of the virus from its native, 160S state to the 135S infective form has therefore been developed. The assay is based on the observation that virus can be efficiently converted to the 135S form in the absence of receptor by heating in hypotonic buffers in the presence of low levels of $Ca^{+2}$.

Figure 9:
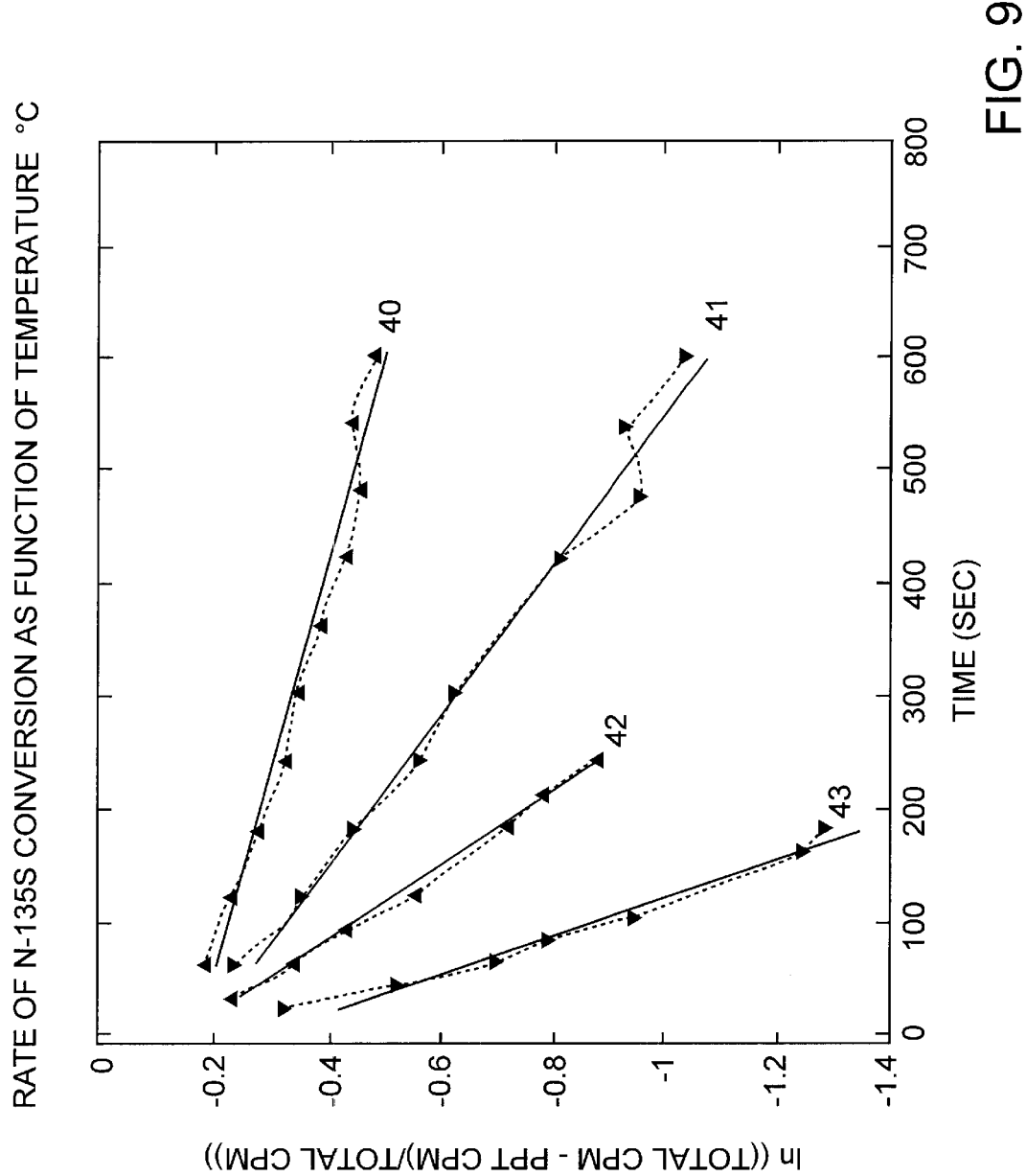
FIG. 9 shows a plot of the results of an immunoprecipitation-based viral inhibition assay.

The assay involves immunoprecipitation using antibodies directed against a peptide corresponding to residues 21–40 of VP1. This region is exposed during the native-135S transition, such that the antibody can only recognize the 135S, and not the native form of the virus. Preliminary studies showed that the rate of conversion of native (unliganded) virus varied steeply as a function of temperature (FIG. 9) and that the rate is significantly reduced by binding drugs with known antiviral activity. The assay measures the rate of conversion at 43° C. where the rates for native virus and virus-R78206 complexes are both within the practical limits of the assay. Briefly, radiolabelled virus is incubated with a compound or library of compounds and then diluted into prewarmed buffer at 43° C. At several time points, aliquots are removed and quenched in chilled buffer. Antisera specific for the amino terminus of VP1 are then added and incubated for 30 min at room temperature. Complexes of antibody with altered virus are then precipitated with protein A beads. The precipitate and supernatant are counted and the first order rate of conversion is calculated from the slope of the best fit line in a plot of log ((total counts—counts precipitated)/total counts) vs time.

Figure 10:
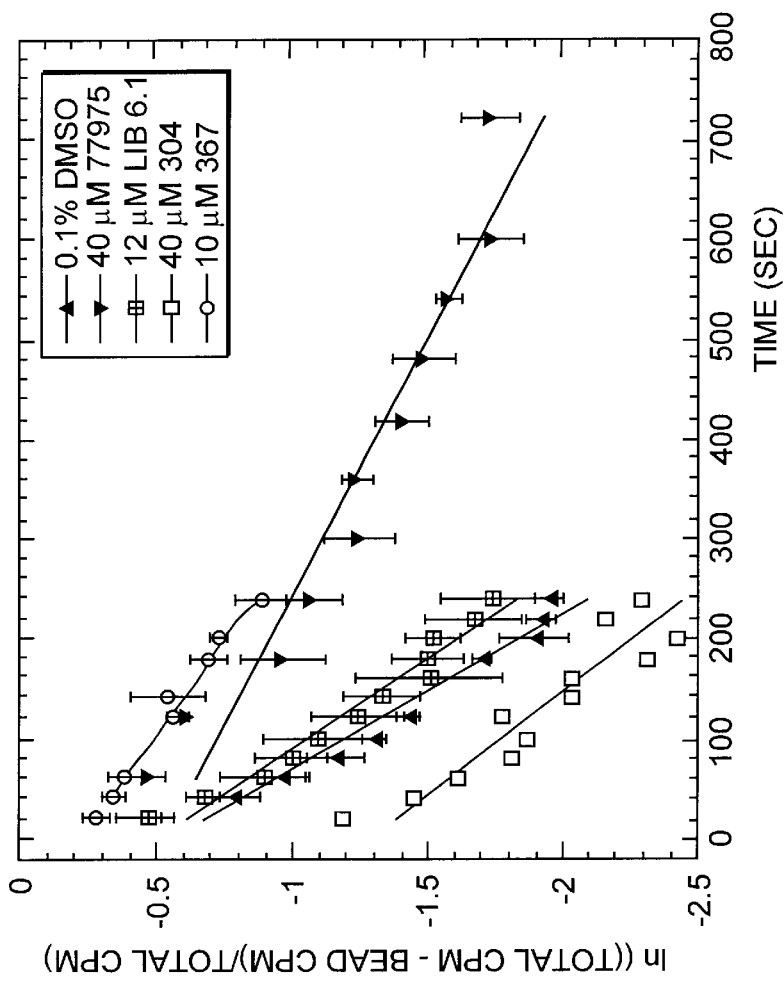
FIG. 10 shows data from a set of viral inhibition assays.
Figure 11:
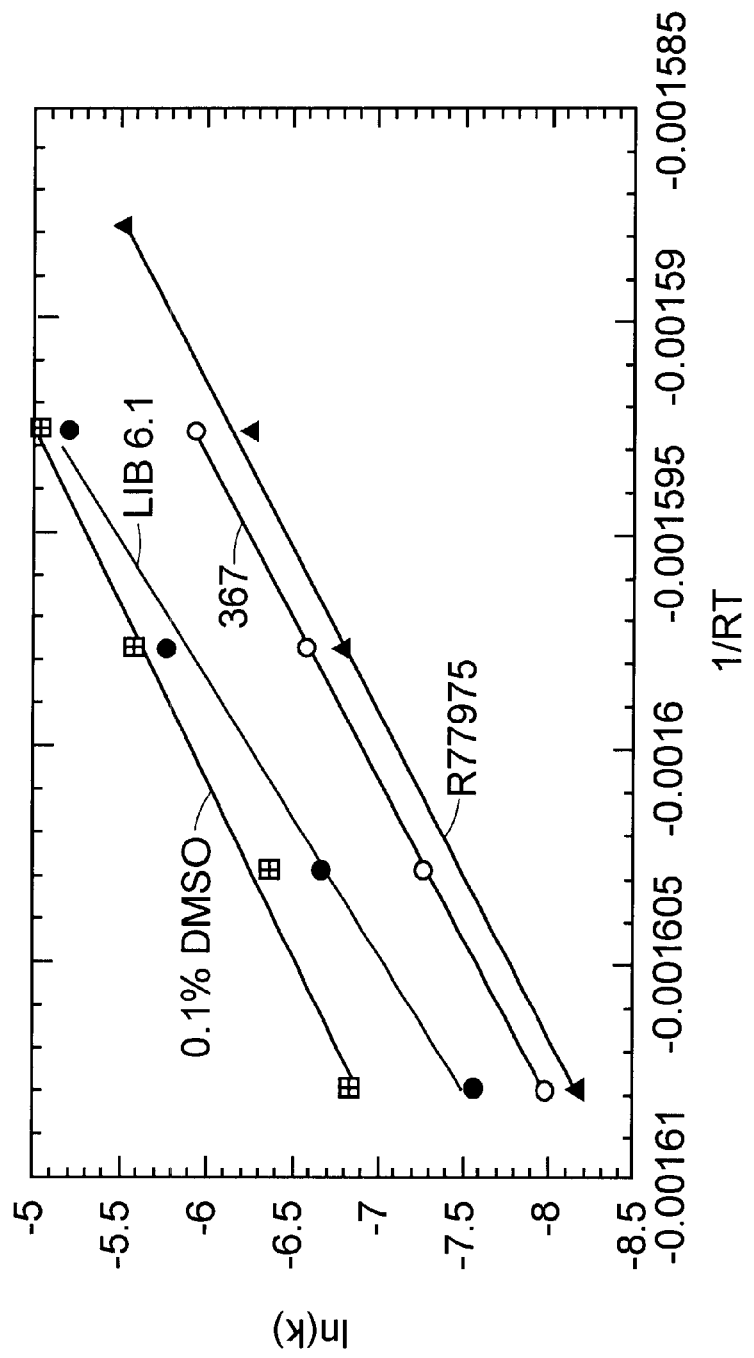
FIG. 11 shows an Arrhenius plot for virus and drug complexes.

The immunoprecipitation assay has been used to characterize the effect of the 6.1 and 6.2 libraries, as well as three individual compounds from the 6.1 library, on the rate of the native- 135S conversion. Two of the purified compounds (304 and 367) had been identified as virus binders in the mass spectroscopy assay. The third (454) was not represented in the library. When synthesized separately the 454 compound was shown to be highly insoluble in most solvents tested, which probably accounts for its failure to be produced in the original library. It was soluble in 0.1% methyl-pyrillodone. Both of the libraries (data for 6.1 are shown) and the 304 and 367 compounds produced modest but highly significant reductions in the rate of conversion at 43° C. (see Table 1 and FIG. 10). The individual compounds 304 and 367 showed more dramatic rate reductions. The rate decrease for the 454 compound is even more impressive (even when the protective effect of the solvent is discounted), and the concentration quoted (50 $\mu$M) is likely to be a gross over estimate of the true concentration of the drug because of its very limited solubility.

H) Crystallographic Assay Confirms Binding in Normal Drug Binding Pocket.

Crystallographic studies of complexes of the candidate ligands with P1/M virus have been performed. To date nearly complete data sets have been collected from crystals soaked in candidate ligands 367 and 304. Data from the 367 complex have been processed, and the structure solved by molecular replacement. The resulting electron density maps clearly show that the ligand is present in the pocket at high occupancy. This confirms that the screening method of the invention is effective in the identification of compounds which bind in the ligand binding pocket of the virus.

I) Stabilization of Virus is Entropically Determined.

The very steep dependence of the first order rate of the native to 135S transition on temperature implies that the activation enthalpy is very high. Indeed, Arrhenius analysis of the dependence of 1n(k) vs 1/RT yields an activation enthalpy of approximately 120kcal/mole (FIG. 11). Previous models for the mechanism of drug action had assumed that the drugs would work by increasing the "stiffness" of the VP 1, thereby increasing the activation enthalpy and decreasing the rate of conversion. However, when similar data are plotted for a variety of virus-complexes, the data fall on parallel lines (FIG. 11), indicating that the enthalpy of activation is identical (or nearly identical) to that of free virus. This means that the predominant effect of drug binding on rate of conversion is entropically derived. Phelps and Post, 1995, J. Mol. Biol. 254: 544, reached a similar conclusion from molecular dynamics simulations of free rhinovirus and rhinovirus drug complexes.

J) Infectivity Inhibition Assay.

The definitive in vitro assay for antiviral activity is an assay that measures a compound's ability to inhibit a virus' ability to lyse cells in culture. A number of variations of this assay have been developed and published. A version of the assay used by Janssen was adapted for use in these screening approaches. Briefly, serial five-fold dilutions of compounds are added directly to a 96 well microtiter plate. Approximately 100 TCID50 of virus is then added to each well and incubated at 37° C. After two hours $10^4$ HeLa cells are added to each well and the plate is incubated for 3 days at 37° C., then stained with crystal violet. The minimum inhibitory concentration is defined as the concentration of drug required to reduce the cytopathic effect by 50%.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

TABLE 1

Rate Constants at 43° C.

| Compound | k($10^{-5}$ s$^{-1}$) |
|---|---|
| 0.1% | 640 ± 23 |
| 40 μM 77975 | 195 ± 3 |
| 12 μM 6 cpd | 550 ± 49 |
| 40 μM 304 | 470 |
| 10 μM 367 | 260 ± 27 |
| 1% methyl-pyrillodone | 269.9 |
| 50 μM 454 | 62.8 |

What is claimed is:

1. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings wherein one of the rings contains a hydroxyl group substituent or a sulfhydryl group substituent, and the spacer monomer is a dibromide spacer monomer and is a symmetric bis-(bromo methyl) arene or alkene, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

2. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and the spacer monomer is a dichloride spacer monomer and is a bis-(chloro methyl) arene or alkene, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

3. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and the spacer monomer is a diiodide spacer monomer and is a bis-(iodo methyl) arene or alkene, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

4. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and the spacer monomer is a ditosylate spacer monomer and is a bis-(tosyl) arene or alkene, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

5. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and one or both of the first aromatic monomer and the second aromatic monomer contains a sulfhydryl group substituent and the spacer monomer is an α, ω dibromo alkane, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

6. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and one or both of the first aromatic monomer and the second aromatic monomer contains a sulfhydryl group substituent and the spacer monomer is an α, ω dichloro alkane, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

7. A method of making a mixture of reaction products from two aromatic monomers and a spacer monomer, wherein the two aromatic monomers are covalently linked through X to the spacer monomer, X is S or O, the aromatic monomer and the spacer monomer are functional group minima of a picornavirus, the two aromatic monomers are selected from the group consisting of single five or six membered rings and fused double rings having a five membered ring and a six membered ring or two six membered rings and wherein one of the rings contains a hydroxyl group substituent or a sulfhydryl group substituent, and one or both of the first aromatic monomer and the second aromatic monomer contains a sulfhydryl group substituent and the spacer monomer is an $\alpha,\omega$ diiodo alkane, comprising the steps of:

mixing a first dissolved aromatic monomer and a second dissolved aromatic monomer to form a mixture, incubating a solution of one or more spacer monomers with the mixture to form an organic phase, washing and concentrating the organic phase.

* * * * *